United States Patent [19]

Ida et al.

[11] 4,301,116

[45] Nov. 17, 1981

[54] SAMPLE TRAY FEEDING APPARATUS FOR USE WITH AN AUTOMATED ANALYZER

[75] Inventors: Hideaki Ida, Musashi-murayama; Toshihide Fujiwara, Fuchu, both of Japan

[73] Assignee: Olympus Optical Co., Ltd., Tokyo, Japan

[21] Appl. No.: 146,368

[22] Filed: May 2, 1980

[30] Foreign Application Priority Data

May 11, 1979 [JP] Japan ................................. 54/57845

[51] Int. Cl.³ .................... G01N 1/10; G01N 1/28; G01N 35/06
[52] U.S. Cl. .................................. 422/65; 422/63; 422/102; 422/104
[58] Field of Search ............. 422/65, 63, 66, 67, 422/64, 102, 104; 141/130; 73/423 A; 221/226, 228–230

[56] References Cited

U.S. PATENT DOCUMENTS

| | | | |
|---|---|---|---|
| 3,533,744 | 10/1970 | Unger | 422/65 X |
| 3,897,216 | 7/1975 | Jones | 422/65 X |
| 4,151,931 | 5/1979 | Scherer et al. | 422/65 X |

*Primary Examiner*—Ronald Serwin
*Attorney, Agent, or Firm*—Cushman, Darby & Cushman

[57] ABSTRACT

A sample tray feeding apparatus comprising a sample tray accommodating container having an opening for inserting sample trays and another opening at the lower end thereof, and a sample tray feeding mechanism for shifting said sample trays from said opening located at the lower end, said sample tray feeding apparatus being so adapted as to accommodate a large number of sample trays in said accommodating container in piled up condition and feed said sample trays consecutively from the lower ones to a sample adhering position through the opening located at the lower end by operating said sample tray feeding mechanism.

2 Claims, 5 Drawing Figures

SAMPLE TRAY FEEDING APPARATUS FOR USE WITH AN AUTOMATED ANALYZER

BACKGROUND OF THE INVENTION (a) Field of the Invention

The present invention relates to a sample tray feeding apparatus be used with automatic electrophoresis apparatus or a similar analytical instrument, and more specifically to a sample tray feeding apparatus so adapted as to prevent samples from being dried.

(b) Description of the Prior Art

There have conventionally been known apparatus which automate in electrophoresis the individual steps such as application of sera onto a carrier made of cellulose acetate paper or the like and forming fractionated patterns through electrical energizing. Among these apparatus, the automatic serum applying apparatus uses an applicator having a large number of blades which are to be inserted into sample trays filled with samples, for example, sera for allowing them to adhere to said blades and then lowered onto a carrier for applying said samples onto said carrier. After the application of the samples, the applicator is shifted into a washing tank for washing off the sera remaining on the blades with washing water and then the washing water adhering onto the blades is removed through drying or by wiped off with filter paper. At the subsequent stages, the above-mentioned steps are repeated for applying other samples successively.

The automatic serum applying apparatus described above uses sample trays (serum trays) having such a construction as shown in FIG. 1. Speaking concretely, the sample tray 1 has an elongated form with numerous cavities 1a formed therein to be filled with samples 2. The samples are successively fed to the adhering position on the applying device by a sample tray feeding apparatus 3 such as shown in FIG. 3. This sample tray feeding apparatus consists of a shifting table 4 having a positioning pin 4a, and functions to set the sample tray 1 at a predetermined position on the shifting table 4 with the pin 4a, shift the table 4 in the direction indicated by the arrow C in FIG. 2 and shift the sample trays consecutively to the adhering position A. Speaking more concretely, a first sample tray 1 located on the left side end in FIG. 2 is shifted first to the position A, applicator 5 having such a construction as shown in FIG. 3 of the serum applying device is brought over the position A and lowered down into the sample tray 1, whereby the blades 5a are dipped into the samples placed in the sample tray 1. The samples are allowed to adhere to the tips of the blades 5a. The blades 5a are thereafter lifted up, shifted in the direction indicated by the arrow D (from the right to the left in the drawing) and then stopped at the applying position B. At this position, the applicator 5 is lowered down to apply the samples onto a carrier 7. After the application of the samples, the carrier is sent to the next stage by an adequate conveying means for forming fractionated patterns of the samples. The applicator is lifted upward and then shifted horizontally to be passed consecutively through a washing tank and drying device (not shown) for washing and drying the blades. The applicator 5 is thereafter shifted rightward to be returned to the position A.

During the step to return the applicator to the position A as described above after the washing and drying, the shifting table 4 of the sample feeding apparatus 3 is shifted leftward in the drawing and the next sample tray is set at the position A. At each of the steps from the sample adhering to blade drying by applying device, the sample trays are consecutively fed to the adhering position by shifting the sample tray feeding apparatus at definite intervals. In the conventional sample feeding apparatus operating as described above, water content is vaporized from the samples for the standby time required after samples are set in the sample feeding apparatus until samples are allowed to adhere to the blades. Since a long time is required from application of a sample onto a carrier to the formation of electrophoretic patterns, a long time must be reserved between adhesion of samples to a blades and that of the next samples. Therefore, the next samples are condensed due to vaporization of water contents from said samples during the standby time. When a sample which is condensed as described above is applied onto a carrier, non-uniformity or disturbance of the application causes adverse effect on analytical result. Vaporization of water content is more remarkable and causes more seriously adverse effect especially on analytical results of samples which are set in later sample trays and require longer standby times.

SUMMARY OF THE INVENTION

A general object of the present invention is to provide a sample tray feeding apparatus so adapted as to accommodate sample trays in a condition where they are piled up on one another, and equipped with a sample tray accommodating container having a sample tray feeding port permitting the lowermost sample tray to pass through said container and a sample tray shifting mechanism for shifting the lowermost sample tray to an adhering position.

DESCRIPTION OF THE PREFERRED EMBODIMENT

Now, the sample tray feeding apparatus according to the present invention will be described detailedly with reference to the embodiment illustrated in the accompanying drawings.

Figure 1:
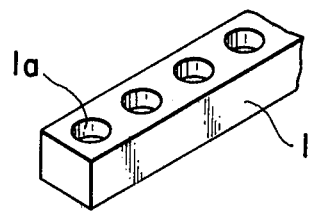
FIG. 1 shows a perspective view of a sample tray.
Figure 4:
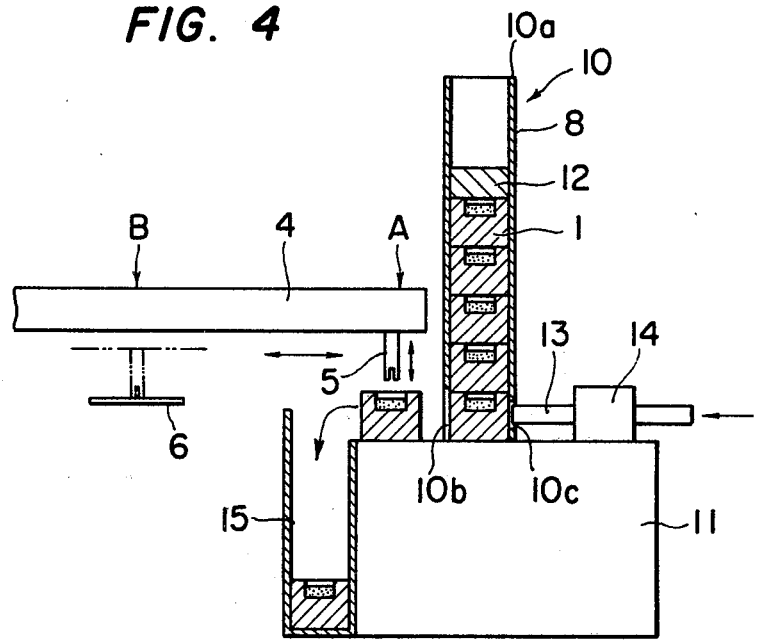
FIG. 4 shows a sectional view illustrating the construction of the sample tray feeding apparatus according to the present invention.

In FIG. 4, the reference numeral 10 represents a sample tray accommodating container which is mounted on a support stand 11 and has the same inside horizontal section as the top surface of the sample tray 1 shown in FIG. 1. Speaking concretely, the sample tray accommodating container has a rectangular sectional shape extremely elongated in one direction. In addition, the sample tray accommodating container has an inside dimentions nearly the same as the outside dimensions of the sample tray 1. Furthermore, the sample tray accommodating container 10 extends in the vertical direction and has an open top end 10a. Therefore, the sample tray 1 can be accommodated into the accommodating container by inserting the former from the top end 10a of the accommodating container 10 with the cavities 1a of the sample tray 1 filled with samples. Formed in one of the side walls on the lower part of the accommodating container is an opening 10b which is a little larger than the side of the sample tray, and in the other side wall is an opening 10c into which a pushing rod can be inserted as described later. The reference numeral 12 represents a plate-like protective cover whose top surface and bottom surface respectively have nearly the same shapes and sizes as the top surface of the sample tray 1, the reference numeral 13 designates a pushing rod, and the reference numeral 14 denotes a piston mechanism which composes the sample tray feeding mechanism together with said pushing rod and other members. The reference numeral 15 represents a receiving container for accommodating the sample trays which have been used for analysis. The sample applicator, etc. remain unchanged from those described with reference to the conventional example.

Figure 2:
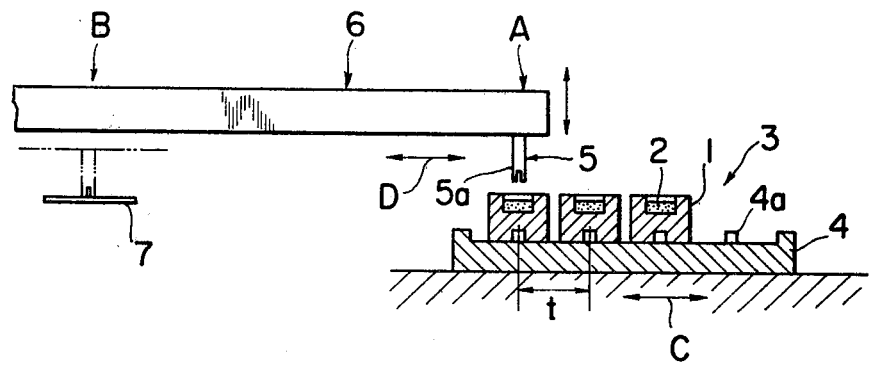
FIG. 2 shows a sectional view illustrating the construction of the conventional sample feeding apparatus.
Figure 3:
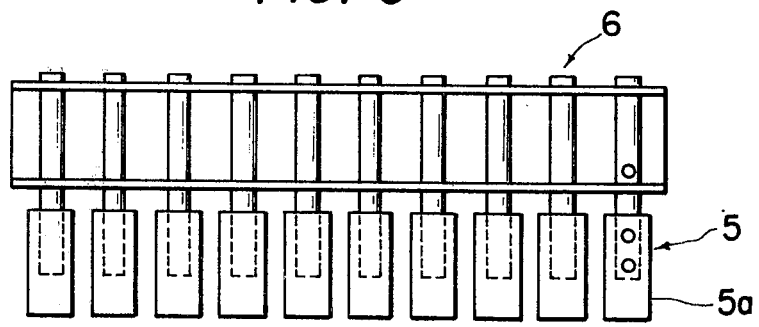
FIG. 3 shows a diagram illustrating an example of sample applicator.

Now, operations of the sample tray feeding apparatus having the above-described construction will be explained below. The sample trays 1 are inserted consecutively into the sample tray accommodating container 10 from the top end 10a thereof as shown in FIG. 4. After a large number of the sample trays 1 have been piled up on one another in the accommodating container 10, the protective cover 12 is inserted into said accommodating container so as to be mounted on the uppermost one of the piled up sample trays. At this stage, the pushing rod 13 is shifted leftward in the drawing by operating the piston mechanism 14 in order to allow the samples to adhere to the applicator. By this operation, the lowermost one of the sample trays 1 which are set in the accommodating container is pushed out through the opening 10b of the container 10 and shifted to the applying position. Then, by returning the pushing rod 13 to its initial position shown in the drawing, the rest sample trays 1 and protective cover 12 go down by their own weights for a distance corresponding to the height of the sample tray into the vacant space left after the lowermost sample tray has been pushed out so that the second lowest sample tray is positioned at the lowermost position in the sample tray accommodating container. On the other hand, the sample applying apparatus performs the same operations as those described with reference to the conventional example shown in FIG. 2, thereby applying the samples filled in the sample tray set in the adhering position A onto a carrier. Successively, the piston mechanism 14 is operated once again so as to push out the second sample tray which is set at the lowermost position and shift it to the adhering position. At this stage, the sample tray which has so far been set at the adhering position A is pushed by the second sample tray and dropped into the receiving container 15. After all the samples have been fed from all the sample trays which were set in the sample tray accommodating container by repeating these operations successively, the protective cover is taken out (can be pushed out with the pushing rod) and then new sample trays are inserted into the sample tray accommodating container. On the other hand, the used sample trays are taken out of the receiving container when it is filed completely. Alternately, the receiving container may be removed in a condition where it still contains the sample trays. Therefore, the receiving container may be fixed to the support stand, but should be removably attached to the support stand for operating convenience in practice.

During the operation of the sample tray feeding apparatus described above, the individual samples set in the sample tray accommodating container are kept in nearly sealed conditions owing to the protective cover 12 and also with the sample trays piled immediately thereover, whereby vaporization of water content from the sample is kept very little. In order to prevent vaporization of water content from the samples more completely, it is desirable that the inside walls of the sample tray accommodating container should have such a construction as to be brought into close contact with the sides of the sample trays.

Figure 5:
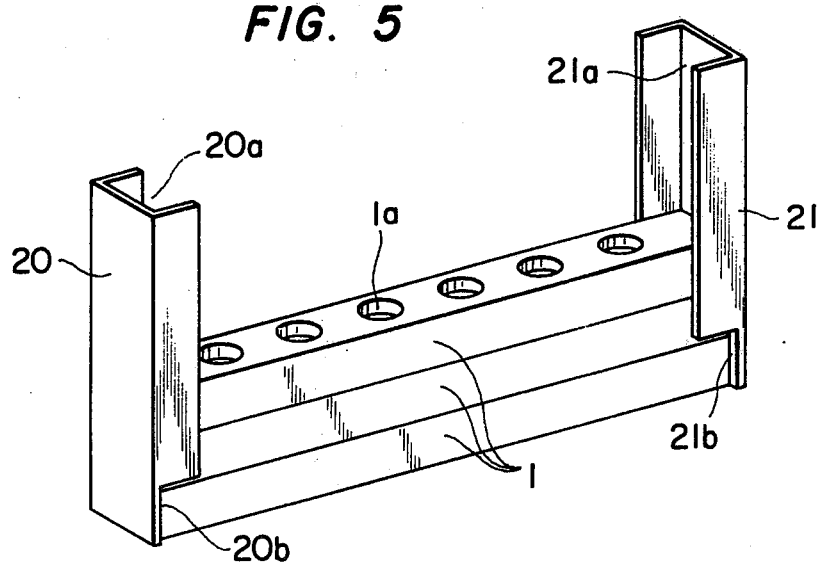
FIG. 5 shows a perspective view illustrating another example of the sample tray accommodating container and other members used in the sample tray feeding apparatus according to the present invention.

FIG. 5 illustrates another example of the sample tray accommodating container. In this example, the accommodating container consists of two holding frames 20 and 21 which have U-shaped sections respectively and are arranged at a definite interval so that the sample trays 1 and the protective cover 12 can be accommodated in piled conditions with their ends fitted into the grooves 20a and 21a of the holding frames 20 and 21. Formed at the lower ends of the holding frames 20 and 21 are notches 20b and 21b for allowing the sample trays to be pushed out of the accommodating container.

This accommodating container has a simple construction consisting only of two fixed holding frames, and reserves a large space between the two frames for facilitating insertion and pushing out of the sample trays.

Though the sample trays feeding apparatus according to the present invention has been described above taking application of samples (sera) onto a carrier in electrophoretic apparatus as an example, the sample tray feeding apparatus is not limited to this use but applicable to sample tray feeding for other types of analyses. As is clear from the foregoing descriptions, the sample tray feeding apparatus according to the present invention can seal samples from external atmosphere during standby time with sample trays piled immediately thereover and the protective cover, thereby preventing water content from being vaporized from the samples and analytical results from being adversely affected due to concentration of the samples.

What is claimed is:

1. A sample tray feeding apparatus comprising a sample tray accommodating container having means to accommodate a large number of sample trays in a condition piled up on one another and to allow only the sample tray located at the lowermost position to be shifted in a lateral direction, each said tray having at least one cavity therein on a first surface thereof, a protective cover for placement on the uppermost one of said sample trays, a sample tray feeding mechanism for shifting said lowermost one of said sample trays to a sample adhering position, each said sample tray having a second surface opposite said first surface thereof shaped so that when said second surface of a said tray engages said first surface on a subjacent tray, said cavity of said subjacent tray will be covered and sealed so as to prevent material in said cavity from evaporating.

2. A sample tray feeding apparatus according to claim 1 wherein said sample tray accommodating container consists of holding frames having U-shaped horizontal sections, notches formed at the lower ends thereof and grooves so arranged as to face each other so that said sample trays can be arranged with both ends thereof fitted into the grooves of said holding frames respectively.

* * * * *